United States Patent [19]

Benz et al.

[11] Patent Number: 4,474,762

[45] Date of Patent: Oct. 2, 1984

[54] ANTIBIOTIC COMPOUNDS, THEIR PRODUCTION AND THEIR MEDICINAL USE

[75] Inventors: Günter Benz, Velbert; Karl G. Metzger, Wuppertal; Jörg Pfitzner, Wuppertal; Delf Schmidt, Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 387,904

[22] Filed: Jun. 14, 1982

[30] Foreign Application Priority Data

Jul. 3, 1981 [DE] Fed. Rep. of Germany ....... 3126389

[51] Int. Cl.$^3$ ................... C07C 103/52; A61K 37/02
[52] U.S. Cl. ............................ 424/177; 260/112.5 R
[58] Field of Search .................. 424/177; 260/112.5 R

[56] References Cited

U.S. PATENT DOCUMENTS 3,450,687 6/1969 Hobbs .......................... 260/112.5 R

FOREIGN PATENT DOCUMENTS 0069882 6/1982 European Pat. Off. .
3102137 8/1982 Fed. Rep. of Germany .
3102136 8/1982 Fed. Rep. of Germany .

*Primary Examiner*—Delbert R. Phillips
*Assistant Examiner*—F. T. Moezie
*Attorney, Agent, or Firm*—Sprung, Horn, Kramer & Woods

[57] ABSTRACT

The invention relates to antimicrobial compounds of Formula (I) and semi-synthetic methods for their production. Also included in the invention are compositions containing said antimicrobial compounds and methods for the use of said compound and compositions.

9 Claims, 6 Drawing Figures

ANTIBIOTIC COMPOUNDS, THEIR PRODUCTION AND THEIR MEDICINAL USE

The present invention relates to new antibiotic compounds, to a semi-synthetic process for their production, and their use as antimicrobial agents in medicine.

It has already been disclosed that a number of compounds of microbial origin possess antimicrobial actions. Some of these antibiotics are not completely satisfactory in their spectrum of action. They frequently exhibit still further disadvantages. $\beta$-Lactam antibiotics are often inactivated by penicillinase, and chloramphenicol, tetracyclines and streptomycin exhibit a considerable number of undesired side effects in many cases (see Walter and Heilmeyer, Antibiotika Fibel (Antibiotics Primer), Georg Thieme Verlag, Stuttgart, 3rd edition, 1969, pages 248, 279–380 and 311–319).

According to the present invention there are provided, as new compounds, antibiotic compounds of the formula in which, X denotes O or $N-CO-NH_2$, $R^1$ denotes an optionally substituted alkyl or cycloalkyl group or an acyl group of the $-CO-R^3$, $R^2$, independently of $R^1$, has any of the meanings given for $R^1$ or denotes a hydrogen atom, and $R^3$ denotes an optionally substituted alkyl, cycloalkyl, aryl or amino group.

Preferred substituents of alkyl and cycloalkyl groups of $R^1$, $R^2$ and $R^3$ are halogen (preferably chlorine), aryl especially mono- or bi-cyclic carbocyclic aryl (preferably phenyl), heteroaryl (preferably heteroaryl radicals have 5 or 6 ring members and preferably containing 1,2 or more N, O and/or S atoms in the ring) and the groups of the formula $COOR^4$, $OR^4$, $SR^4$ and $NR^4$, in which $R^4$ denotes hydrogen and/or optionally substituted alkyl, cycloalkyl or aryl.

Preferred substituents of alkyl or cycloalkyl groups of $R^4$ are the abovementioned substituents of alkyl and cycloalkyl. Likewise preferred substituents on the aryl and heteroaryl radicals are those substituents of alkyl mentioned above.

Preferred alkyl groups, herein, are open-chain linear or branched alkyl having up to 6 carbon atoms and preferred cycloalkyl groups have 3 to 7 (especially 5 or 6) carbon atoms.

Preferred aryl and heteroaryl groups are, respectively, phenyl, pyridyl or furanyl.

If the radicals mentioned are substituted, 1, 2 or 3 substituents are preferred.

Compounds of Formula (I) according to the present invention, in which

X denotes O or $N-CO-NH_2$, $R^2$ denotes a hydrogen atom, and $R^1$ denotes the acyl radical of an amino acid or of a di- to pentapeptide, are preferred.

Also preferred are compounds of Formula (I) in which $R^1$ represents an alkyl group having up to 6 carbon atoms and compounds in which $R^3$ represents an alkyl group having up to 6 carbon atoms.

Particularly preferred compounds of Formula (I) are those in which X has the meaning $N-CO-NH_2$ and $R^1$ and $R^2$ have the following meanings:

| $R^1$ | $R^2$ | |
|---|---|---|
| $CH_3$ | $CH_3$ | |
| $CH_3\!\!\diagdown\!\!CH-CH-CO-$<br>$CH_3\!\!\diagup\quad\ \ \|$<br>$\qquad\quad\ NH_2$ | H | (2) |
| $C_2H_5$ | $C_2H_5$ | |
| $n\text{-}C_3H_7$ | $n\text{-}C_3H_7$ | |
| $n\text{-}C_4H_9$ | $n\text{-}C_4H_9$ | |
| $CH_3-CO-$ | H | |
| $C_2H_5-CO-$ | H | |
| $C_3H_7-CO-$ | H | |
| $CH_3-O-CH_2-CO-$ | H | (4) |
| $F\text{-}\langle\phantom{O}\rangle\text{-}CH_2-$ | H | |
| $NH_2-CO-$ | H | |
| $CH_3\!\!\diagdown\!\!CH-CH_2-CH-CO-$<br>$CH_3\!\!\diagup\qquad\qquad\ \|$<br>$\qquad\qquad\qquad\ NH_2$ | H | |
| $HO_2C-CH_2-CH_2-CO-$ | H | |
| $H_2N\diagdown\!\!{}^{\displaystyle CH_2\text{-}C_6H_{11}}\!\!\diagup CO-$ | H | |
| $H_2N\diagdown\!\!{}^{\displaystyle CH(OH)}\!\!\diagup CO-$ | H | |
| $H_2N\diagdown\!\!{}^{\displaystyle CH(CH_3)}\!\!\diagup CO-$ | H | (1) |
| $H_2N\diagdown\!\!{}^{\displaystyle D}\!\!\diagup CO-$ (cyclohexyl) | H | |
| $n\text{-}C_4H_9-CO-$ | H | |
| $CH_3\!\!\diagdown\!\!CH-CO-$<br>$CH_3\!\!\diagup$ | H | |
| cyclohexyl-$(CO_2H)$-$CO-$ | H | |

-continued

| R¹ | R² |
|---|---|
| CH₃\<br>    CH—CH₂—CH—CO—<br>CH₃/                 NH₂<br>                D | H |
| CH₃—CH₂—CH—CH—CO<br>           CH₃ NH₂ | H |
|         H<br>CH₂—CO—N—CH₂—CO—<br>H₂N | H (3) | as well as compounds in which X=O and R¹ and R² have the following meanings:

| R¹ | R² |
|---|---|
| CH₃\     NH₂<br>   CH—CH—CO—<br>CH₃/ | H |
| CH₃ | CH₃ |
| F—⟨◯⟩—CH₂— | H |
| n-C₃H₇ | n-C₃H₇ |
| CH₂—CO—N—CH₂—CO—<br>H₂N | H |

(The numbers (1), (2), (3) and (4), above, are used to identify R¹ and R² substituents in those compounds referred to later in Table 9).

The novel compounds of the present invention have a powerful antimicrobial, e.g. antibacterial action.

According to the present invention there is further provided a process for the production of a compound of the present invention in which (i) a compound of formula (I) in which both R¹ and R² represent hydrogen atoms is produced by growing Streptomyces spec. WS 116 (DSM 1692), or a mutant or variants derived therefrom, under submerse, aerobic conditions in a nutrient medium containing assimilable carbon, nitrogen and mineral salts (preferably including iron salts), at a temperature of 15° to 35° C., and the compounds formed are isolated from the fermentation liquid and are separated, and (ii) the compound of formula (I) in which X has the required meaning, thus obtained, is reacted at the free amino group to substitute the said amino group by the required radical R¹, or radicals R¹ and R².

The strain streptomyces spec. WS 116 from the order of the actinomycetales, family streptomycetaceae, genus streptomyces, or variants and mutants derived from this strain, can be employed for the preparation process. This strain was isolated from a marine soil sediment sample from the Ibero-Canary Sea. It was deposited in the Deutsche Sammlung für Mikroorganismen [German Collection of Microorganisms], Göttingen, under the number DSM 1692 on 7.12.1979.

(a) The spores are ellipsoidal. They have the dimensions 0.4–0.7×0.7–1.2μ and a smooth surface.

(b) The colour of the sporulated mycelium is chalk-white at the beginning and yellowish in the mature state (griseus type).

(c) The spore chains are straight or undulating (rectus flexibilis type) and monopodially branched.

(d) No black-brown pigment was formed on peptone-iron agar and on tyrosin agar. The strain is not chromogenous.

The collected characteristics identify the strain WS-116 as belonging to the type streptomyces griseus Waksman and Henrici.

Nutrient medium used in step (i) for the preparation of the mixture of the compounds contain the customary carbon and nitrogen sources and the necessary salts.

The following can be used as a carbon source: carbohydrates, in particular polysaccharides, such as starch or dextrins, disaccharides, such as maltose or cane sugar, monosaccharides, such as glucose or xylose, sugar alcohols, such as mannitol or glycerol, carboxylic acids, such as citric acid, maleic acid, acetic acid or mixtures thereof, and in addition naturally occurring mixtures, such as malt extract.

Surprisingly, the highest active compound yields were obtained with carboxylic acids, in particular citric acid, as the main carbon source.

The customary nitrogen sources include, for example, proteins, albumin hydrolysation products, amino acids (such as glutamic acid, aspartic acid, argenine, lysine, ornithine or serine) and in addition nucleoside bases (such as cytosine, or uracil) ammonium salts, nitrates and especially, naturally occurring complexes, such as peptones, corn steep liquor, soya bean meal, meat extracts, yeast extracts and suitable mixtures of these substances.

Particularly high yields of active compound are obtained when L-ornithine and L-serine in the ratio of 3:1, for example 0.3% and 0.1%, in a sterile-filtered form, are added to the medium with the customary complex N sources.

The necessary salts include mineral salts, such as phosphates, sulphates, carbonates, nitrates or chlorides of sodium, potassium, calcium, magnesium, iron, zinc, copper, molybdenum, cobalt, nickel and manganese.

The presence of about 0.01% of FeCl₃ has proved to be desirable. Some of the mineral salts, including the FeCl₃, are contained as constituents, in the necessary concentrations, in the abovementioned carbon or nitrogen sources or in the water used.

Furthermore, anti-foaming agents of the most diverse type, such as soya bean oil, polyols or silicones, can also be used as auxiliaries.

Water may be mentioned as the most important diluent for the nutrient media.

The preparation process is carried out under aerobic or micro-aerophilic conditions; the culture can be carried out according to customary methods, for example using shaken cultures or aerated fermenter cultures, in the customary batch or fed batch process. The percentage proportions (percentages by weight in each case) of the nutrient solution constituents can vary within wide ranges, and in general the carbon sources comprise in total 0.5 to 8%, preferably 0.6 to 6%, and the nitrogen sources comprise in total 0.05 to 4%, preferably 0.5 to 2%; the salts are present in customary concentrations, preferably in the range between 0.001 and 0.5% by weight. The anti-foaming agent is present in a concentration of 0 to 1%. The temperatures used for sterilisation are from 100° to 140° C., preferably from 120° to 130° C., and sensitive substances, such as amino acids, are sterile-filtered.

The pH values of the growing cultures are between 5 and 10, preferably between 6 and 9.5. The culture temperature can be between 15° and 35° C., preferably between 20° and 30° C. It has been found that the amount of the products concentrated in the culture broth in general reaches its maximum about 1 to 10, preferably about 2 to 5, days after the beginning of culture. The end point of the fermentation is determined with the aid of biological tests. (Action against *E. coli* in a customary agar diffusion test).

The compounds obtained are isolated from the culture filtrate by extraction with mixtures of phenol/chloroform or by adsorption on active charcoal or on suitable resins. It is advantageous to bind the compounds to non-specific adsorber resins based on polystyrene (for example "Amberlite" XAD (Trade Mark) of Rohm & Haas or "Lewatite" OC 1031 (Trade Mark) of Bayer). It has been found that the compounds are particularly firmly bonded by resins of this type when iron salts, in particular iron chloride, are added in concentrations of 0.05 to 0.2, in particular approx. 0.1 g/liter of culture broth, before the adsorption process. The adsorption is carried out in the pH range 3 to 9, in particular in the range 5 to 7. The desorption of the compounds is carried out fractionally using mixtures of water and organic solvents, in particular water/methanol. The active fractions are combined, concentrated to a small volume, and lyophilised. A 0.5 to 3% strength by weight crude product which contains the compounds is obtained.

Starting from this crude product, further concentration of the compounds can be carried out by a combination of anion exchange chromatography (for example DEAE-"Sephadex" A 25 (Trade Mark), Pharmacia) or cation exchange chromatography) for example SP- or CM-"Sephadex" C 25, Pharmacia). A 30 to 50% strength by weight preparation is obtained by this means, since accompanying peptides are not separated off. These peptides can be separated off by adsorption chromatography or partition chromatography of the approx. 30 to 50% strength by weight compound over silica gel in the system isobutanol/ethanol/25% concentrated ammonia=9/1/5 (Parts by volume).

However, this separation process is associated with substance losses.

The separation can be carried out in a substantially simpler manner by affinity chromatography in an $Fe^{+++}$-containing column. For this purpose, a cation exchanger based on polystyrene resin or acrylic resin (for example "Dowex" 50 WX 4 (Trade Mark), DOW Chemical) or based on polydextran (for example "Sephadex" C 25, Pharmacia) is converted into the $Fe^{+++}$ form with $FeCl_3$ solution. The solution of the crude product is now introduced onto the resin in the $Fe^{+++}$ form, and the resin is then rinsed with water. The column is eluted with a buffer of high ionic strength, for example 0.2M $NaH_2PO_4$/0.3M NaCl. This buffer elutes the bulk of the inactive accompanying peptides. The active substances are then eluted from the column using the same buffer, but with the addition of 0.05M ethylenediaminetetraacetic acid or another iron complex-former (for example citrate). The active fractions are combined and are introduced over a column containing a non-specific adsorber resin (for example "Lewatit" OC 1031, Bayer), whereby the active substances are bonded. The column is eluted with methanol, and the eluate is concentrated and lyophilised.

The compounds of reaction step (i) with $R^1$ and $R^2$=H may be obtained in pure form by partition chromatography over "Sephadex" G 25/n BuOH/iso BuOH/0.2M $(NH_4)_2SO_4$=2/1/1. The purification of the products is further carried out by simple chromatography of the active compound mixture over a CM cellulose column in the $H^+$ form, using distilled water without any additives. The eluate, collected in fractions, is lyophilised.

These two compounds can occur in the iron-containing form (complexed) and in the iron-free form. The iron-free compound with X=O ("Component A") can be characterised as follows:

(1) The elementary analysis C 43.8%; H 6.7%; N 14.1%; O 30.3%; and S 4.1%.

It must be pointed out here that in the case of higher molecular weight natural products the range of error of the elementary analysis can be greater than is generally customary, and an exact determination of the empirical formula is therefore often impossible (R. B. Woodward, Angew. Chem. 69, pages 50–51 (1957)).

(2) The freeze-dried compound melts between 180° and 185° C. and decomposes on further warming.

(3) Ultraviolet absorption spectrum:

The UV spectrum was recorded for an aqueous solution of the compound (c=2.863 mg in 50 ml of $H_2O$). The spectra in acid (or basic) solution were measured on a solution which was prepared by the addition of 100 microliters of 1N hydrochloric acid (or sodium hydroxide solution) to 3 ml of the above solution.

TABLE 1

Maxima ($\lambda$ max) and extinctions $\left[ E \frac{1\%}{cm} \right]$ of the compound

| | $\lambda$ max [m$\mu$] | $\left[ E \frac{1\%}{cm} \right]$ |
|---|---|---|
| neutral | 267 | 103 |
| acid | 267 | 97.10 |
| basic | — | — |

Figure 1:
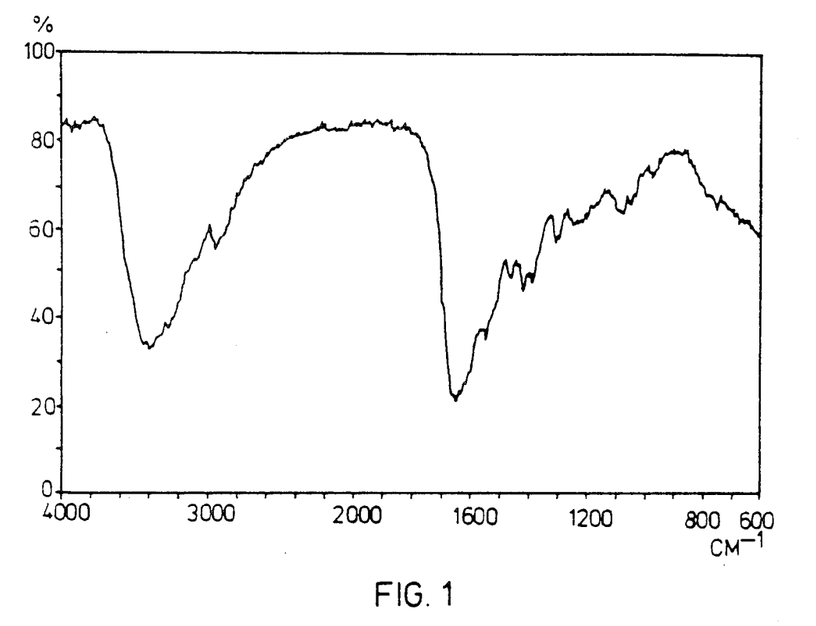

(4) The IR absorption spectrum of the compound is represented in FIG. 1 (abscissa: wave number in $cm^{-1}$, ordinate: absorption)

When the substance is pressed to give KBr discs, it shows absorption bands at the following wavelengths (expressed in $cm^{-1}$):

TABLE 2

| Wavelengths of the IR absorption spectrum | |
|---|---|
| Wavelength in $cm^{-1}$ | Wavelength in $cm^{-1}$ |
| 3384 | 1210 |
| 2918 | 1160 |
| 1654 | 1090 |
| 1615 | 970 |
| 1540 | |
| 1457 | |
| 1415 | |
| 1390 | |
| 1300 | |
| 1240 | |

Figure 2:
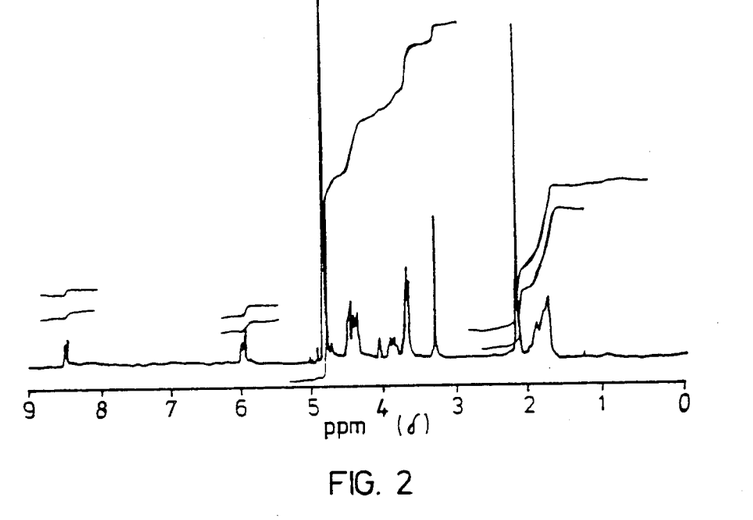

(5) The $^1H$ nuclear resonance spectrum gives the signal position in parts per million (ppm) and oscillations per second, according to FIG. 2. It was recorded for an aqueous solution of the compound using the Na salt of TMS as a standard (external), on a WH-360 spectrometer of Bruker at a field strength of 360 MHZ.

(6) The 13-C nuclear resonance spectrum was recorded on a WM 250 spectrometer of Bruker at a field strength of 62.71 MHZ, for an aqueous solution of the compound, the values being converted to be based on dioxan as the external standard (shift position 67 400 ppm relative to TMS=O).

Figure 3:
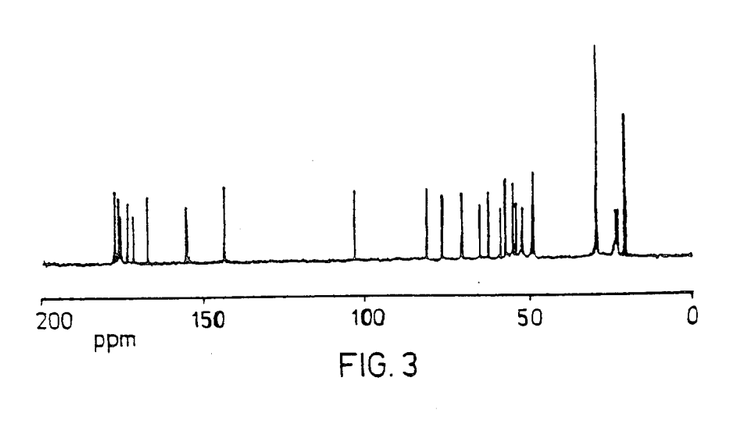

The 13-C nuclear resonance spectrum according to FIG. 3 shows the relative intensities of the following signals, given in parts per million (ppm) and oscillations per second (HZ):

TABLE 3

Shift positions and intensities of the signals in the 13-C nuclear resonance spectrum based on dioxan - 67.400 ppm (external)

| Signal NS | relative intensity | signal position (ppm) |
|---|---|---|
| 1 | 11.061 | 20.222 |
| 2 | 2.101 | 20.511 |
| 3 | 3.960 | 22.305 |
| 4 | 4.026 | 23.173 |
| 5 | 3.867 | 23.364 |
| 6 | 16.325 | 28.919 |
| 7 | 4.636 | 47.906 |
| 8 | 6.720 | 48.097 |
| 9 | 4.263 | 51.317 |
| 10 | 4.490 | 53.464 |
| 11 | 4.625 | 54.302 |
| 12 | 5.906 | 54.45 |
| 13 | 6.302 | 56.346 |
| 14 | 4.260 | 58.317 |
| 15 | 5.171 | 61.993 |
| 16 | 4.332 | 64.581 |
| 17 | 5.260 | 70.022 |
| 18 | 5.100 | 75.962 |
| 19 | 5.436 | 80.536 |
| 20 | 5.437 | 102.328 |
| 21 | 5.790 | 142.604 |
| 22 | 4.421 | 153.765 |
| 23 | 5.004 | 166.249 |
| 24 | 3.694 | 170.322 |
| 25 | 4.663 | 171.837 |
| 26 | 3.740 | 174.028 |
| 27 | 3.837 | 174.395 |
| 28 | 5.046 | 174.778 |
| 29 | 2.662 | 174.925 |
| 30 | 5.686 | 175.792 |

(7) The optical rotation is $[\alpha]_D^{20} = -20.216$ (C=0.3951% in water).

(8) The compound has an unrestricted solubility in water, dissolves slightly in methanol, dimethylformamide and dimethylsulphoxide, and is sparingly soluble in chloroform, ether, ethylacetate and petroleum ether.

(9) The compound is a colourless, amorphous solid, the aqueous solution of which has a neutral reaction.

(10) The $R_f$ values of the compound in the iron-free and iron-containing form in comparison with other compounds in various mobile phases are given in Table 4.

(a) Instant thin layer chromatography sheets silica gel 60 F 254 (Merck)

colouration: 1. ninhydrin; 2. 5% $FeCl_3 \times 6 H_2O$ in 0.5N HCl mobile phase 1 (MP 1): isobutanol/ethanol/ammonia=9/1/5 mobile phase 2 (MP 2): isobutanol/ethanol/ammonia=4/1/5

10 cm length of run/charge 50 μg in distilled water

TABLE 4a

| Substance | MP 1 | MP 2 |
|---|---|---|
| Neomycin sulphate | 0.01 | 0.16 |
| 2-Desoxystreptamine × 2 HCl | 0.03 | 0.19 |
| Sisomicin base | 0.14 | 0.42 |
| Compound, iron-free | 0.02 | 0.26 |
| Compound, iron-containing | 0 | 0.23 |

(b) Instant thin layer chromatography plates cellulose F (Merck)

colouration: 1. ninhydrin, 2. 5% $FeCl_3 \times 6H_2O$ in 0.5N HCl mobile phase 1 (MP 1): butan-1-ol/glacial acetic acid/distilled water 4/1/5 mobile phase 2 (MP 2): butan-1-ol/glacial acetic acid/distilled water 4/1/2 mobile phase 3 (MP 3): propan-1-ol/pyridine/glacial acetic acid/distilled water 15/10/3/12

10 cm length of run/charge 50 μg in distilled water.

TABLE 4b

| Substance | MP 1 | MP 2 | MP 3 |
|---|---|---|---|
| Neomycin sulphate | 0.06 | 0.06 | 0.06 |
| 2-Desoxystreptamine × 2 $H_2O$ | 0.10 | 0.13 | 0.42 |
| Sisomicin base | 0.16 | 0.27 | 0.49 |
| Compound, iron-free | 0.37 | 0.42 | 0.83 |
| Compound, iron-containing | 0.14 | 0.25 | 0.74 |

(11) The compound, in its iron-free form, can be made visible on the thin layer sheet with $FeCl_3$(*), alkaline potassium permanganate, iodine or ninhydrin, and in UV light at 254 or 280 nm by fluorescence extinction.
(*)The spray reagents are prepared according to customary instructions (for example E. Stahl Dünnschichtchromatographie [Thin layer chromatography] 2nd edition, Springer Verlag, Berlin).

The compound with X=N—CO—$NH_2$ ("Component B") can be characterised in the iron-free form as follows:

(1) Elementary analysis C 42.3%; H 6.2%; N 15.7%; O 31.4%; and S 3.6%.

(2) The freeze-dried compound decomposes at about 185° C.

(3) Ultraviolet absorption spectrum:
The UV spectrum was recorded for an aqueous solution of the compound (c=1.786 mg in 25 ml of $H_2O$). The spectra in acid (or basic solution) were measured for a solution which was prepared by the addition of 100 microliters of 1N hydrochloric acid (or sodium hydroxide solution) to 3 ml of the above solution.

TABLE 5

Maxima (λ max) and extinctions $E \frac{1\%}{cm}$ of the compound

| | λ max [mμ] | $\left[ E \frac{1\%}{cm} \right]$ |
|---|---|---|
| neutral | 282 | 123 |
| acid | 304 | 108 |
| basic | 277 | 118 |

Figure 4:
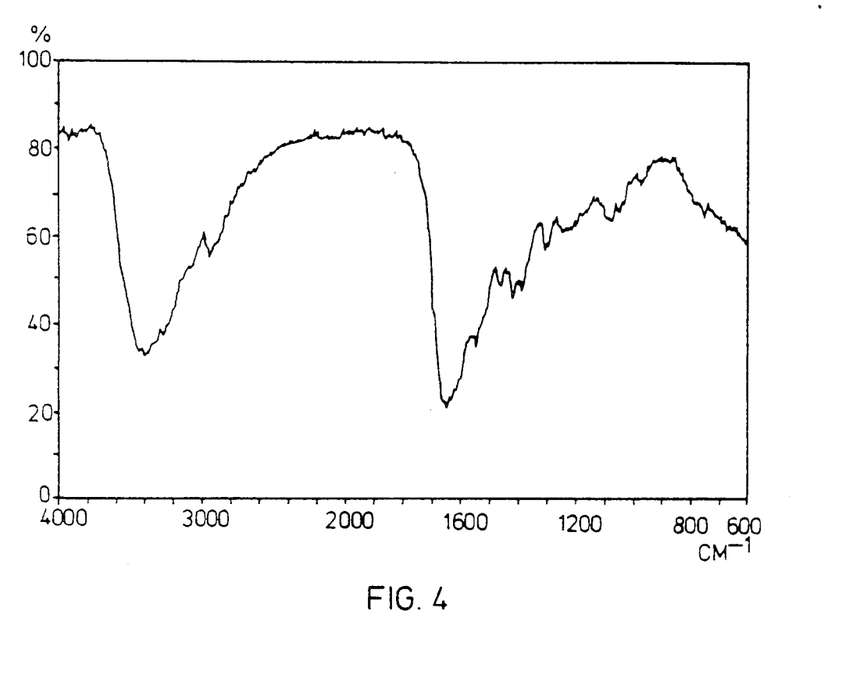

(4) The IR absorption spectrum of the compound is represented in FIG. 4. (Abscissa: wave number in $cm^{-1}$, ordinate: absorption).

When the substance is pressed to give KBr discs, it shows absorption bands at the following wavelengths (expressed in $cm^{-1}$):

TABLE 6

| Wavelength in cm⁻¹ | Wavelength in cm⁻¹ |
| --- | --- |
| 3388 | 1070 |
| 2944 | 1050 |
| 1695 | 975 |
| 1648 | |
| 1545 | |
| 1457 | |
| 1417 | |
| 1390 | |
| 1299 | |
| 1240 | |

Figure 5:
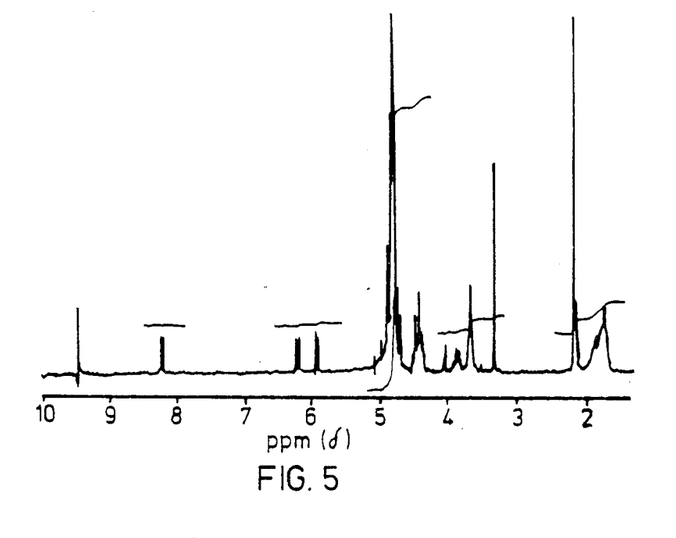

(5) The $^1$H nuclear resonance spectrum gives the signal position in parts per million (ppm) and oscillations per second, according to FIG. 5. It was recorded for an aqueous solution of the compound using the Na salt of TMS as a standard (external), on a WH-360 spectrometer of Bruker at a field strength of 360 MHZ.

(6) The 13-C nuclear resonance spectrum was recorded on a WM-250 spectrometer of Bruker at a field strength of 62.71 MHZ for an aqueous solution of the compound, the values being converted to be based on dioxan as the external standard (shift position 67.400 ppm relative to TMS=O).

Figure 6:
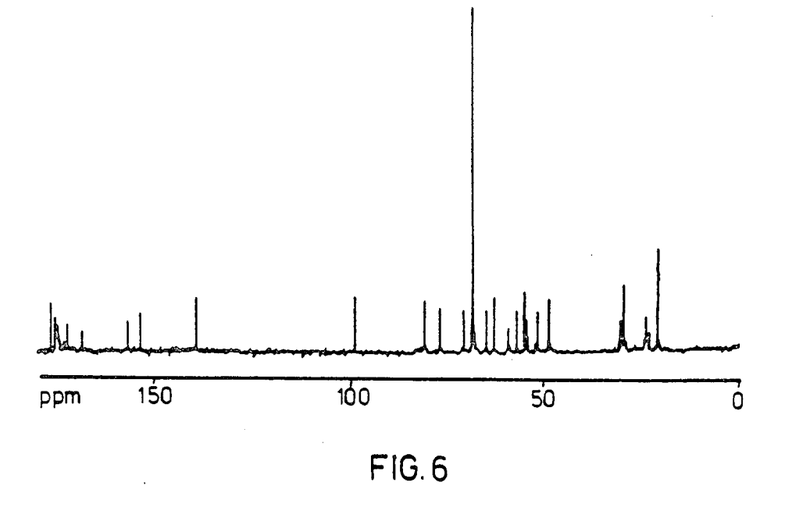

The 13-C nuclear resonance spectrum according to FIG. 6 shows the relative intensities of the following signals, given in parts per million (ppm) and oscillations per second (HZ):

TABLE 7

Shift positions and intensities of the signals in the 13-C nuclear resonance spectrum based on dioxan = 67.400 ppm (external)

| Signal NS | relative intensity | signal position (ppm) |
| --- | --- | --- |
| 1 | 3.344 | 175.878 |
| 2 | 2.094 | 174.610 |
| 3 | 1.628 | 174.289 |
| 4 | 1.634 | 174.032 |
| 5 | 1.708 | 171.786 |
| 6 | 1.25 | 167.843 |
| 7 | 1.966 | 156.220 |
| 8 | 2.580 | 153.171 |
| 9 | 3.806 | 138.745 |
| 10 | 3.979 | 98.082 |
| 11 | 3.729 | 80.173 |
| 12 | 3.207 | 76.001 |
| 13 | 3.044 | 69.984 |
| 14 | 83.487 | 67.400 |
| 15 | 2.996 | 64.094 |
| 16 | 4.082 | 62.072 |
| 17 | 1.751 | 58.606 |
| 18 | 2.995 | 56.392 |
| 19 | 4.129 | 54.418 |
| 20 | 4.430 | 54.322 |
| 21 | 2.449 | 54.017 |
| 22 | 2.983 | 51.064 |
| 23 | 3.998 | 48.111 |
| 24 | 2.442 | 29.834 |
| 25 | 4.590 | 29.048 |
| 26 | 5.047 | 28.967 |
| 27 | 2.559 | 23.319 |
| 28 | 2.276 | 23.223 |
| 29 | 1.510 | 22.634 |
| 30 | 7.743 | 20.222 |

(7) The optical rotation immediately after dissolving is $[\alpha]_D^{20} = -27.725°$ (c=0.2723% in water).

(8) The compound has an unrestricted solubility in water, dissolves slightly in methanol, dimethylformamide and dimethylsulphoxide, and is sparingly soluble in chloroform, ether, ethylacetate and petroleum ether.

(9) The compound is a colourless, amorphous solid, the aqueous solution of which has a neutral reaction.

(10) The $R_f$ values of the compound in the iron-free and iron-containing form in comparison with other compounds in various mobile phases are given in Table 8.

(a) Instant thin layer chromatography sheets silica gel 60 F 254 (Merck)

colouration: 1. ninhydrin; 2. 5% $FeCl_3 \times 6H_2O$ in 0.5N HCl mobile phase (MP 1): isobutanol/ethanol/ammonia=9/1/5 (parts by volume)

mobile phase 2 (MP 2): isobutanol/ethanol/ammonia=4/1/5 (parts by volume)

10 cm length of run/charge 50 µg in distilled water

TABLE 4a

| Substance | MP 1 | MP 2 |
| --- | --- | --- |
| Neomycin sulphate | 0.01 | 0.16 |
| 2-Desoxystreptamine × 2 HCl | 0.03 | 0.19 |
| Sisomicin base | 0.14 | 0.42 |
| Compound, iron-free | 0.02 | 0.26 |
| Compound, iron-containing | 0 | 0.23 |

(b) Instant thin layer chromatography sheets cellulose F (Merck)

colouration: 1. ninhydrin; 2. 5% $FeCl_3 \times 6HCl$ mobile phase 1 (MP 1): butan-1-ol/glacial acetic acid/distilled water 4/1/5 mobile phase 2 (MP 2): butan-1-ol/glacial acetic acid/distilled water 4/1/2 mobile phase 3 (MP 3): propan-1-ol/pyridine/glacial acetic acid/distilled water 15/10/3/12

10 cm length of run/charge 50 µg in distilled water

TABLE 8b

| Substance | MP 1 | MP 2 | MP 3 |
| --- | --- | --- | --- |
| Neomycin sulphate | 0.06 | 0.06 | 0.06 |
| 2-Desoxystreptamine × 2 H₂O | 0.10 | 0.13 | 0.42 |
| Sisomycin base | 0.16 | 0.27 | 0.49 |
| Compound, iron-free | 0.27 | 0.33 | 0.80 |
| Compound, iron-containing | 0.15 | 0.19 | 0.71 |

(11) The compound, in its iron-free form, can be made visible on the thin layer sheet with $FeCl_3$*, alkaline potassium permanganate, iodine or ninhydrin, and in UV light at 254 or 280 nm by fluorescence extinction.

These compounds in the iron-free form are converted into their derivatives at the terminal amino group of the ornithine in which $R_1$ has a meaning given above and, if desired, in which $R_2$ has a meaning given, other than hydrogen.

The corresponding monoalkyl and dialkyl compounds can be obtained by reductive alkylation with aliphatic and aromatic aldehydes and sodium cyanoborohydride in a slightly acid aqueous medium.

The acylations can be effected under modified Schotten-Baumann conditions, in a neutral aqueous-alcoholic medium, using a carboxylic acid anhydrides.

The aminoacylations can be effected using peptides or L- and D-amino acids protected with o-nitrophenyl-sulphenyl (NPS) or t-butoxycarbonyl (BOC), after activation via the mixed anhydrides or the active esters.

The components A and B are employed in an unprotected form in all reactions.

The purification can be effected by chromatography over cellulose ion exchangers and over silica gel.

The good antimicrobial activity of the compounds according to the invention is demonstrated by in vitro test of the following Example A.

In the agar dilution test according to the internationally customary test (American National Committee for Clinical Laboratory Standards=NCCLS), in vitro activity was found against the germs listed below.

TABLE 9

| Compound* | Germ | MIC µg/ml |
|---|---|---|
| (1) | E. coli Neumann | ≦0.06 |
|  | Staph. aureus 1756 | ≦0.06 |
| (2) | E. coli Neumann | ≦0.01 |
|  | Staphylococcus aureus 133 | ≦0.01 |
| (3) | E. coli Neumann | ≦0.06 |
|  | Klebsiella 57 US | ≦0.06 |
| (4) | E. coli Neumann | ≦0.06 |

(*see numbers identifying specific compounds in the previously tabulated particularly preferred compounds of the present invention).

The determination of the minimum inhibiting concentration (MIC) was effected with an inoculator by the agar dilution method, using a sowing density of $10^4$ per inoculation point. The MIC is the concentration at which no bacteria colonies grow.

The compounds according to the invention are active against a broad spectrum of micro-organisms. They can be used to combat Gram-negative and Gram-positive bacteria and bacteria-like micro-organisms and to prevent, ameliorate and/or heal illnesses caused by these pathogens.

The active compounds according to the invention are particularly active against bacteria and bacteria-like microorganisms. They are therefore particularly suitable for the prophylaxis and chemotherapy of local and systemic infections, caused by these pathogens, in human medicine and veterinary medicine.

For example, local and/or systematic illnesses caused by the following pathogens or by mixtures of the following pathogens can be treated and/or prevented:

Micrococcaceae, such as Staphylococci, for example *Staphylococcus aureus*, (Staph.=Staphylococcus);

Enterobacteriaceae, such as Escherichiae bacteria of the Coli group: Escherichia bacteria, for example *Escherichia coli*, Enterobacter bacteria, for example *E. aerogenes* and *E. cloacae*, Klebsiella bacteria, for example *K. pneumoniae*, *K. pneumoniae* and *K. ozaenae*, Erwiniae, for example Erwinia spec., Serratia, for example *Serratia marcescens* (E.=Enterobacter) (K.=Klebsiella).

Pseudomonadaceae, such as Pseudomonas bacteria, for example *Pseudomonas aeruginosa* (Ps.=Pseudomonas).

As stated above, the invention also relates to the use in medicine antimicrobial agents of the compounds of the invention.

The present invention provides a pharmaceutical composition containing as active ingredient a compound of the invention in admixture with an inert pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally.

In general it has proved advantageous to administer amounts of from 0,1–50 mg/kg (especially 1–10 mg/kg) of body weight per day to achieve effective results. Nevertheless, it can at times be necessary to deviate from those dosage rates, and in particular to do so as a function of the nature and body weight of the warm-blooded animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

Processes for the production of compounds according to the present invention are illustrated by the following Examples in which Example 1 illustrates process step (i). The product of process step (i) in which X denotes O is referred to hereinafter as "component A" and the product of process step (i) in which X denotes N—CO—NH$_2$ is referred to hereinafter as "component B".

EXAMPLE 1

Preparation of the compounds with $R^1=R^2=H$ (a) The nutrient solution in which the production strain streptomyces spec. WS 116 was cultivated in the precultures was composed of 2% by weight of glucose, 1.3% of yeast extract, 0.05% of a polyol and tap water. The pH was adjusted to 6.5 before the sterilisation. 4 1,000 ml Erlenmeyer flasks, each of which contained 150 ml of this nutrient solution, were inoculated with the production strain and incubated for 4 days at 28° C. on a rotary shaking machine at 220 revolutions per minute. These precultures were used to inoculate a second preculture in a laboratory fermenter which contained 20 liters of the nutrient solution, and this preculture was incubated for 3 days at 25° C., at 200 revolutions per minute and 10 liters of air per minute. 10 liters of this culture were used to inoculate a production fermenter which contained 600 ml of nutrient solution having the following compositon: 0.7% by weight of citric acid, 0.8% of yeast extract, 0.2% of de-fatted soya bean meal, 0.2% of corn steep liquor and 0.05% of a silicone in tap water. The pH of this nutrient solution was adjusted to 6.4 with potassium hydroxide solution, before sterilisation. The incubation of the production culture was effected over 2 to 4 days at 25° C. and a rate of stirring of 100 revolutions per minute and an aeration of only 50 liters of air per minute. The fermentation was stopped at the optimum antibiotic inhibiting activity of the culture.

(b) 2×150 ml of a preculture as in Example 1 (a) were cultivated. These precultures are used to inoculate 10 liters of a production fermenter, the nutrient solution of which, made up in tap water, had the following composition: 0.7% by weight of citric acid, 0.8% by weight of yeast extract, 0.2% by weight of de-fatted soya bean meal, 0.2% by weight of corn steep liquor, 0.3% by weight of L-ornithine, 0.1% by weight of L-serine and 0.05% by weight of a silicone.

All constituents except for ornithine and serine were sterilised in a culture vessel in a customary manner. A pH value of 6.4 was established before sterilisation, ornithine and serine, dissolved in distilled H₂O, were added in a sterile-filtered form to the mixture.

The incubation of the production culture was effected over 2 to 4 days at 25°, at a rate of stirring of 200 revolutions per minute and an aeration of only 1.5 liters of air per minute. The fermentation was stopped at the optimum antibiotic inhibiting activity of the supernatant culture.

(c) 4,000 liters of culture broth (pH=9.06) were adjusted to pH 6.2 with 50 liters of 1:1 dilute HCl. 400 g of FeCl₃. 6H₂O were added, the mixture was stirred, and 25 liters of dilute NaOH were then added, whilst stirring, until the pH was 7. The mixture was then separated in a Westfalia separator at 200 to 250 l/h. The supernatant liquid was introduced through a 30×70 cm high column filled with "Lewatit" OC 1031 (=nonspecific adsorber resin of BAYER AG), and the permeate was discarded as effluent since it was inactive. The column was washed with 1,000 liters of deionised water, and the inactive washing water was discarded. The column was then washed with 1,000 liters of 15% methanol, and this inactive wash liquor was also discarded. The activity was then eluted from the column with 50% methanol and 100 liter fractions were collected. The active eluates 2 and 3 were combined, concentrated into approximately 20 liters in a thin-film evaporator, and then lyophilised. 342 g of crude product with a purity of approximately 2.5% were obtained.

(d) The above crude substance was dissolved in 6 liters of H₂O, and 25 ml of a 50% strength FeCl₃ solution was added, whilst stirring. The precipitate which formed was centrifuged off after having been stirred for 15 minutes (Hettich Rota Magna centrifuge, 1.5 liter beaker, 30 minutes, 4,000 rpm). The supernatant liquid was introduced under gravity over a 8×45 cm high column filled with SP-"Sephadex" C 25 Fe +++. The flow rate was 4 liters per hour. The black coloured column was rinsed with 5 liters of distilled water, followed by 10 liter of 0.2M NaH₂PO₄/0.3M NaCl buffer. The permeate and wash liquor contained less than 5% of the input antibiotic activity. The column, which was now only pale brown coloured, was then eluted with 0.2M NaH₂PO₄/0.3M NaCl/0.05M EDTA (flow rate 2-3 l/h), the column eluate was collected fractionally in 500 ml portions. The active fractions 6 to 14 were combined and introduced over a 4×40 column filled with "Lewatit" OC 1031. The flow rate was 3 l/h. The column was then washed with distilled water until, using AgNO₃, Cl⁻ could no longer be detected in the column eluate (approx. 6 liters, flow rate 5 l/h). The column was then eluted with 3 liters of 90% methanol, which were collected in batches, concentrated, and lyophilised. Yield: 6.74 g: 82.6% (both components).

(e) Half the yield from Example 1 (c)=3.37 g were dissolved in 100 ml of distilled water. The conductivity was 210 μS.

This solution was introduced onto a 5×30 cm column filled with CM cellulose in H⁺ form (CM Cellulose C 52, Whatmann). The column was developed with distilled water at a flow rate of 840 ml/h. The eluate was divided on the basis of the refraction curve, conductivity curve and extraction curve. First runnings (inactive) of 980 mg were obtained.

Fraction 1: 427 mg
Fraction 2: 674 mg
Fraction 3: 363 mg
Fraction 4-6: 475 mg
Fraction 7: 253 mg
Fraction 8: 96 mg Fraction 1 is component A.
The fractions 2 to 8 contain component B.

EXAMPLE 2

N-Dimethylamino derivative of component B 100 mg (0.1 mmol) of component B (obtained as described in Example 1) were dissolved in 2 ml of water and 0.5 ml of acetonitrile and 0.1 ml of 37% aqueous formaldehyde solution was added. After a drop of glacial acetic acid had been added, 19 mg (0.3 mmol) of sodium cyanoborohydride were added in portions at 25° C., and the mixture was stirred for 16 hours. The solution was concentrated, and separated over a Merck instant column size A (240-10) "Lichropep" Si60 (Trade Mark). A gradient of acetonitrile:water 4:1→2:1 was used as the mobile phase. The uniform fractions were freeze-dried.

Yield 56.7 mg (55.5%).

¹H-NMR (D₂O 250 MHz): δ=1.50–1.98 (m;12H,B,γ-CH₂—Ornithine), 2.15 (s; 9H, N-acetyl), 2.67 (s; 6H, —N(CH₃)₂), 3.34 (s; 3H, >N—CH₃), 5.94 (d, J=6 Hz; 1H, H-1'), 6.22 (d, J=8 Hz; 1H, H-5), 8.20 (d, J=8 Hz; 1H, H-6). UV (qualitative, pH 1): $\lambda_{max}$=304 nm.

EXAMPLE 3

N-Dimethylamino derivative of component A 50 mg (0.052 mmol) of component A (obtained as described in Example 1) were dissolved in 1 ml of water and 0.25 ml of acetonitrile, and 0.05 ml of a 37% aqueous formaldehyde solution was added. After a drop of glacial acetic acid had been added, 9.5 mg of sodium cyanoborohydride were added in portions at 25° C., and the mixture was stirred for 16 hours. The solution was concentrated, and chromatographed over 7.5 g of silica gel (0.063/0.2 mm). A gradient of acetonitrile:water 9:1→2:1 was used as the mobile phase. The uniform fractions were freeze-dried.

Yield: 16 mg (31.4%).

¹H-NMR(D₂O,250 MHz): δ=1.49–1.92 (m; 12H, β,γ-CH₂—ornithine), 2.13 (s; 9H, N-acetyl), 2.56 (s; 6H, —N(CH₃)₂), 3.29 (s; 3H, >N—CH₃), 5.94 (d, J=6 Hz; 1H,H-1'), 5.98 (d, 8 Hz; 1H, H-5), 8.42 (d, J=8 Hz; 1H, H-6).

UV (qualitative, pH 1): $\lambda_{max}$=266 nm.

EXAMPLE 4

N-Methoxyacetyl derivative of component B 200 mg (0.2 mmol) of component B (obtained as described in Example 1) were suspended in 10 ml anhydrous methanol. After 2 ml of methoxy acetic acid anhydride has been added, the mixture was stirred for 16 hours at 25° C., the pH being kept at 7 with triethylamine. 200 ml of anhydrous diethyl ether were then added to the mixture. The ethereal solution was discarded, and the precipitated product was stirred for 30 minutes with 10 ml of 0.5N ammonia/methanol, and concentrated in a rotary evaporator. The residue was chromatographed over 20 g of silica gel (0.063 to 0.2 mm). A gradient of acetonitrile:water 9:1→8:2 was used as the mobile phase.

Yield: 115.8 mg (54.4%).

¹H-NMR(D₂O,250 MHz): δ=1.56–1.92 (m; 12H, β,γ-CH₂—ornithine), 2.14 (s; 9H, N-acetyl), 3.33 (s; 3H, >N—CH₃), 3.43 (s; 3H, O—CH₃), 4.05 (s; 2H, —OCH- 2—CO), 5.94 (d, J=6; 1H, H-1'), 6.22 (d, J=8 Hz, 1H, H-5), 8.22 (d, J=8 Hz; 1H, H-6).

UV (qualitative, pH 1): $\lambda_{max}$=304 nm.

EXAMPLE 5

N-Succinyl derivative of component B 50 mg (0.05 mmol) of component B (obtained as described in Example 1) were suspended in 2 ml of anhydrous methanol. After 250 mg (2.5 mmol) of succinic acid anhydride have been added, the mixture was stirred for 16 hours at 25° C. The product was precipitated with 100 ml of anhydrous diethyl ether and filtered off. The residue was stirred for 10 minutes with 5 ml 1N ammonia/methanol at 25° C., and the solution was concentrated, and chromatographed over 5 g of silica gel (0.063-0.2 mm). A gradient of acetonitrile:water 4:1→2:1 was used as the mobile phase.

Yield: 28 mg (51.0%).

$^1$H-NMR($D_2O$, 250 MHz): $\delta$=1.58-1.92 (m; 12H, $\beta,\gamma$-$CH_2$—ornithine), 2.14 (s; 9H, N-acetyl), 2.52 (s; 4H, —$CH_2$— succinic acid), 3.32 (s; 3H>N—$CH_3$), 5.95 (d, J=6 Hz; 1H, H-1'), 6.22 (d, J=8 1H, Hz; H-5), 8.22 (d, J=8 Hz; 1H, H-6).

UV qualitative, pH 1): $\lambda_{max}$=304 nm.

EXAMPLE 6

N-L-Valyl derivative of component B 50 mg (0.05 mmol) of component B (obtained as described in Example 1) and 183.5 mg (0.5 mmol) of N-o-nitrophenylsulphenyl-L-valine N-hydroxy-succinimide ester were added to 4 ml of water:tetrahydrofuran 1:1, and the mixture was stirred for 16 hours at 25° C., the pH being adjusted to 7 with 0.1N triethylamine. The mixture was evaporated to dryness in a bulb tube. The residue was extracted three times with 10 ml of diethyl ether. The ethereal phase was discarded, and the residue was stirred for 30 minutes at 25° C. in a solution of 4 ml of methanol, 0.4 ml of glacial acetic acid and 0.4 ml 1N sodium thiosulphate solution. The resulting mixture was filtered, 10 ml of water were added to the filtrate, and the mixture was extracted three times with 10 ml of diethyl ether. The aqueous phase was freeze-dried, and chromatographed over 10 g of silica gel (0.063-0.2 mm). Acetonitrile:water 8:2 was used as the mobile phase.

Yield: 5.2 mg (9.5%).

$^1$H-NMR/$D_2O$, 250 MHz): $\delta$=0.97 (d broad, J=6 Hz; 6H, —$CH_3$ valine), 1.55-1.89 (m; 12H, $\beta,\gamma$—$CH_2$—ornithine), 2.13 (s; 9H, N-acetyl), 3.31 (s; 3H; >N—$CH_3$), 5.94 (d, J=6 Hz; 1H, H-1'), 6.20 (d, J=8 Hz; 1H, H-5), 8.20 (d, J=8 Hz; 1H, H-6).

UV (qualitative, pH 1): $\lambda_{max}$=303 nm.

EXAMPLE 7

N-L-Valyl derivative of component A 50 mg (0.052 mmol) of component A (obtained as described in Example 1) and 95.4 mg (0.26 mmol) of N-o-nitrophenylsulphenyl-L-valine N-hydroxy-succinimide ester were added to 5 ml of water:tetrahydrofuran 1:1. The pH was adjusted to 7 with 0.1N triethylamine solution, and the mixture was stirred for 16 hours at 25° C. The resulting solution was concentrated in a rotary evaporator (40° C.), and the residue was extracted twice with 10 ml of diethyl ether. The ethereal phase was discarded, and the residue was stirred for 60 minutes at 25° C. in a solution of 3 ml of methanol, 0.3 ml of glacial acetic acid and 0.3 ml of 1N sodium thiosulphate solution. The resulting suspension was diluted with 10 ml of water and filtered, and the filtrate was extracted twice with 10 ml of ether. The aqueous phase was freeze-dried, and chromatographed over 7.5 g of silica gel (0.063-0.2 mm). Acetonitrile:water 4:1 was used as the mobile phase.

Yield: 9.5 mg (17.4%).

$^1$H-NMR ($D_2O$, 250 MHz): $\delta$=0.96 (d broad, J=6 Hz; 6H, —$CH_3$ valine), 1.56-1.94 (m; 12H, $\beta,\gamma$-$CH_2$—ornithine), 2.13 (s; 9H, N-acetyl), 3.29 (s; 3H, N—$CH_3$), 5.96 (d, J=6 Hz; 1H, H-1'), 5.99 (d, J=8 Hz; 1H, H-5), 8.49 (d, J=8 Hz; 1H, H-6).

UV (qualitative, pH 1): $\lambda_{max}$=264 nm.

EXAMPLE 8

N-L-Alanyl derivative of component B 50 mg (0.05 mmol) of component B (obtained as described in Example 1) and 84.8 mg (0.25 mmol) of N-o-nitrophenylsulphenyl-L-alanyl N-hydroxy-succinimide ester were dissolved in 5 ml of water:tetrahydrofuran 1:1. The pH was adjusted to 7 with 0.1N triethylamine solution. After 16 hours, the mixture was concentrated at 40° C. in a rotary evaporator, and the residue was extracted twice with 10 ml of diethyl ether. The ethereal phase was discarded, and the residue was stirred for 60 minutes at 25° C. in a solution of 3 ml of methanol, 0.3 ml of glacial acetic acid and 0.3 ml of sodium thiosulphate. The resulting suspension was diluted with water and extracted three times with 10 ml of diethyl ether, and the aqueous phase was freeze-dried. The crude material was chromatographed over 7.5 g of silica gel (0.063 to 0.2 mm). Acetonitrile:water 4:1 was used as the mobile phase.

Yield: 13.9 mg (26.1%).

$^1$H-NMR ($D_2O$, 250 MHz): $\delta$=1.50 (d; J=7 Hz; 3H, CH-$CH_3$—alanine); 1.58-1.92 (m; 12H, $\beta,\gamma$-$CH_2$—ornithine); 2.14 (s; 9H, N-acetyl), 3.32 (s; 3H, N—$CH_3$); 5.94 (d; J=6 Hz; 1H, H-1'); 6.20 (d; J=8 Hz; 1H, H-5); 8.20 (d; J=8 Hz; 1H, H-6).

UV (qualitative, pH 1): $\lambda_{max}$=305 nm.

EXAMPLE 9

N-Glycyl-glycyl derivative of component B 300 mg (0.3 mmol) of component B (obtained as described in Example 1) and 494 mg (1.5 mmol) of t-butoxycarbonylglycylglycyl N-hydroxysuccinimide ester were dissolved in 60 ml of water:tetrahydrofuran 1:1. After 101 mg (1.2 mmol) of sodium bicarbonate had been added, the mixture was stirred for 20 hours at 25° C. The mixture was concentrated at 40° C. in a rotary evaporator, and the residue was stirred with 10 ml of methylene chloride/trifluoroacetic acid 1:1 for 30 minutes at 0° C. The solution was concentrated, the residue was taken up in 10 ml of water, and the solution was adjusted to pH 7 with 1N sodium hydroxide solution. Salts were removed from the solution over 30 ml of adsorber resin OC 1031, and, after freeze drying, the solution was chromatographed over 15 g of silica gel (0.06-0.2 mm). A gradient of acetonitrile:water 9:1→1:1 was used as the mobile phase.

Yield: 200.2 mg (60.3%).

$^1$H-NMR ($D_2O$, 250 MHz): $\delta$=1.59-1.89 (m; 12H, $\beta,\gamma$-$CH_2$—ornithine), 2.12 (s; 9H, N-acetyl), 3.31 (s; 3H, N—$CH_3$), 3.65 (m; 6H, $\delta$-$CH_2$ ornithine), 3.82 (s; 2H, $\alpha$-$CH_2$, glycine), 4.01 (s; 2H, $\alpha$-$CH_2$ glycine), 5.94 (d, J=6 Hz; 1H, H-1'), 6.20 (d, J=8 Hz; 1H, H-5); 8.21 (d, J=8 Hz; 1H, H-6).

UV (qualitative, pH 1): $\lambda_{max}=304$ nm.

EXAMPLE 10

N-Glycyl-glycyl derivative of component A

The quantity of mixture and the method of carrying out the preparation were as in Example 9.

Yield: 222.8 mg (66.4%).

$^1$H-NMR (D$_2$O, 250 MHz): $\delta=1.55$–1.89 (m; 12H, $\beta,\gamma$-CH$_3$— ornithine), 2.12 (s; 9H, N-acetyl), 3.28 (s; 3H, N—CH$_3$), 3.78 (s; 2H, $\alpha$-CH$_2$ glycine), 4.01 (s; 2H, $\alpha$-CH$_2$ glycine), 5.94 (d, J=6 Hz; 1H, H-1'), 5.98 (d, J=8 Hz; 1H, H-5), 8.48 (d, J=8 Hz; 1H, H-6).

UV (qualitative, pH 1): $\lambda_{max}=266$ nm.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:

1. A compound of the formula in which

X denotes O or N—CO—NH$_2$,

R$^1$ is C$_1$–C$_6$-alkyl or C$_3$–C$_7$-cycloalkyl which is optionally substituted by halogen, heteroaryl having 5 or 6 ring members and containing 1 or 2N, O or S atoms, phenyl which is optionally substituted by halogen or COOR$^4$, OR$^4$, SR$^4$ or NR$^4$ —COOR$^4$, OR$^4$, SR$^4$ or NR$^4$ or is

R$^3$—CO—

R$^2$, independently of R$^1$, has any of the meanings given for R$^1$ or denotes a hydrogen atom R$^3$ is an amino group or phenyl or has the meaning of R$^1$ R$^4$ is hydrogen or C$_1$–C$_6$-alkyl, C$_3$–C$_7$-cycloalkyl or phenyl, all optionally substituted by halogen heteroaryl having 5 or 6 ring members and containing 1 or 2N, O or S atoms phenyl which may be substituted by halogen, COOalkyl (C$_1$–C$_6$), O-alkyl (C$_1$–C$_6$), S-alkyl (C$_1$–C$_6$) or N-alkyl (C$_1$–C$_6$), COOH, OH, SH, NH$_2$ COOH, OH, SH, NH$_2$, C$_1$–C$_6$-alkyl-O—, C$_1$–C$_6$alkyl-S—, C$_1$–C$_6$-alkyl-N— or C$_1$–C$_6$alkyl-OOC.

2. A compound according to claim 1, in which R$^1$ represents an alkyl group up to 6 carbon atoms.

3. A compound according to claim 1 or 2, in which that R$^3$ represents an alkyl group having up to 6 carbon atoms.

4. A pharmaceutical composition containing as an active ingredient an antibacterially effective amount of a compound according to claim 1 in admixture with an inert pharmaceutical carrier.

5. A pharmaceutical composition of claim 4 in the form of a sterile or physiologically isotonic aqueous solution.

6. A composition according to claim 4 containing from 0.5 to 95% by weight of the said active ingredient.

7. A medicament in dosage unit form comprising an antibacterially effective amount of a compound according to claim 1 and an inert pharmaceutical carrier.

8. A medicament of claim 7 in the form of tablets, pills, dragees, capsules, ampoules, or suppositories.

9. A method of combating bacterial infections in warm-blooded animals which comprises administering to the animals an antibacterially effective amount of an active compound according to claim 1, either alone or in admixture with a diluent or in the form of a medicament.

* * * * *

UNITED STATES PATENT AND TRADEMARK OFFICE
CERTIFICATE OF CORRECTION

PATENT NO. : 4,474,762

DATED : October 2, 1984

INVENTOR(S) : Gunter Benz et al

It is certified that error appears in the above-identified patent and that said Letters Patent is hereby corrected as shown below:

Col. 2, lines 42, 55 and 65  Delete "  " and substitute

Col. 10, line 15  Delete "Table 4a" and substitute --Table 8a--

Col. 10, lines 19, 20 under column MP 2  Delete "0.26" and "0.23" and substitute respectively --0.25-- and --0.22--

Col. 16, line 22  After "$D_2O$" insert -- , --

Col. 16, line 29  Center "N-Dimethylamino derivative of component A"

Col. 16, line 46  After "5.98(d," insert --J= --

Col. 16, line 55  Delete "has" and substitute --had--

Signed and Sealed this

Thirtieth Day of April 1985

[SEAL]

Attest:

DONALD J. QUIGG

Attesting Officer   Acting Commissioner of Patents and Trademarks